United States Patent
Postma

(10) Patent No.: US 7,432,813 B2
(45) Date of Patent: *Oct. 7, 2008

(54) METHOD AND SYSTEM FOR DETERMINING HARDWARE CONFIGURATION OF MEDICAL EQUIPMENT USING RF TAGS

(75) Inventor: Steve Postma, New Berlin, WI (US)

(73) Assignee: General Electric Company, Niskayuna, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/949,579

(22) Filed: Dec. 3, 2007

(65) Prior Publication Data

US 2008/0083824 A1    Apr. 10, 2008

Related U.S. Application Data

(63) Continuation of application No. 10/723,717, filed on Nov. 26, 2003, now Pat. No. 7,304,573.

(51) Int. Cl.
    G08B 13/14    (2006.01)
    G06F 17/00    (2006.01)
    G06Q 10/00    (2006.01)

(52) U.S. Cl. .................. 340/572.1; 700/115; 705/28

(58) Field of Classification Search .............. None
    See application file for complete search history.

(56) References Cited

U.S. PATENT DOCUMENTS 5,562,621 A    10/1996    Claude et al.
5,861,019 A    1/1999    Sun et al.
6,557,758 B1    5/2003    Monico
6,724,308 B2    4/2004    Nicholson
6,935,560 B2    8/2005    Andreasson et al.
7,158,030 B2    1/2007    Chung
2002/0181944 A1    12/2002    Kawahara et al.
2003/0033280 A1    2/2003    Van Den Hamer et al.
2003/0038721 A1    2/2003    Hogan
2003/0135246 A1    7/2003    Mass et al.
2003/0160698 A1    8/2003    Andreasson et al.
2004/0024730 A1    2/2004    Brown et al.
2004/0162586 A1    8/2004    Covey et al.
2006/0197787 A1    9/2006    Kusunoki et al.

FOREIGN PATENT DOCUMENTS

JP    2002049900    2/2005
WO    WO00005674    2/2000
WO    WO0209016    1/2002
WO    WO0231629    4/2002
WO    WO03026558    4/2003
WO    WO03071943    9/2003

*Primary Examiner*—Julie Lieu
(74) *Attorney, Agent, or Firm*—Fletcher Yoder

(57) ABSTRACT

According to one embodiment, the present technique provides a medical device component having an RF tag that is configured to provide information regarding the medical device component. Particularly, the RF tag may contain and provide information regarding maintenance, installation, and manufacture of the medical device component. Indeed, the exemplary embodiment of the present technique may facilitate the development of an "as built" or hardware configuration of the medical device through the use of RF tags. Advantageously, the medical device may be surveyed by activating the RF tags, which contain and transmit information regarding the various components in the medical device.

21 Claims, 4 Drawing Sheets

METHOD AND SYSTEM FOR DETERMINING HARDWARE CONFIGURATION OF MEDICAL EQUIPMENT USING RF TAGS

CROSS REFERENCE TO RELATED APPLICATION

This application is a continuation of U.S. patent application Ser. No. 10/723,717, entitled "METHOD AND SYSTEM FOR DETERMINING HARDWARE CONFIGURATION OF MEDICAL EQUIPMENT USING RF TAGS", filed Nov. 26, 2003, which is herein incorporated by reference.

BACKGROUND

The present technique relates to methods and apparatus for servicing and maintaining medical equipment. More particularly, the present technique relates to servicing and maintaining medical equipment via radio frequency tags.

Medical practitioners, such as physicians, may employ various types of medical devices to diagnose and treat patients. As one example, imaging devices, such as magnet resonance imaging (MRI) devices, positron emission tomography (PET) devices, computed tomography (CT), or X-ray systems, may produce detailed images of internal tissues and organs of a patient, thereby mitigating the need for invasive exploratory procedures and providing valuable tools for identifying and diagnosing disease and for verifying wellness.

Such medical devices may include any number of components and sub-systems for operation. However, from time to time, the various components and sub-subsystems require maintenance and/or replacement. For example, the performance of the components may degrade over time, thereby reducing the efficacy of the medical device. To restore the medical device to its full potential, a technician may adjust or service the various components. In certain instances, the technician may replace the component in question with a new component all-together.

Typically, records related to the maintenance of the medical device are entered manually. For example, the technician may create a record of the service event manually by entering information regarding the service event into a logbook. However, a follow-up technician (i.e., subsequent technician) may not have access to the previously created record. Accordingly, the follow-up technician may not have access to information regarding the components in the medical device. Difficulties in servicing the medical device may arise if the technician lacks information regarding the components presently in the medical device, i.e., a current hardware configuration. For example, if a manufacturer issues a recall on a certain component, the technician may find it difficult to locate the particular medical devices in need of recall service. Similarly, with no record or inaccurate records of service events, hardware or software configurations, service technicians may be required to spend valuable time to determine the existing equipment and programming present in the system before being able properly to perform servicing. Difficulties in obtaining information regarding the components of a medical device may lead to increased costs and delays.

Accordingly, there is a need for an improved technique for maintaining and servicing medical devices. Particularly, there is a need for a technique that provides information regarding components of a medical device to reduce costs, delays, and difficulties in servicing and maintaining medical devices.

BRIEF DESCRIPTION

The present invention provides techniques for addressing such needs. According to one embodiment, the present technique provides an assembly for use with medical device. The assembly includes a component configured for operation with the medical device, such as a programmable logic unit (PLU) in a heart monitor, an X-ray detector, a cryogenic cold head, medical device control circuitry, to name but a few examples. The assembly also includes a radio frequency (RF) transmitter configured to transmit information about the component. By way of example, a technician may survey the medical device to determine its present configuration via an RF reader, which receives the RF transmissions from the various RF transmitters located throughout the medical device, particularly on the components.

According to another embodiment, the present technique provides an imaging device system. The system includes an imaging device, which may be one of any number of imaging devices. The system also includes a component that is operable with the imaging device and that is located in the imaging device. Furthermore, the system includes an RF transmitter configured to broadcast information about the component.

Additionally, the present technique provides an exemplary method for maintaining a medical device. The method includes activating an RF device having information regarding at least one of maintenance, installation, and manufacture of a component of the medical device. The method also includes receiving the information regarding the component via a transmission from the RF device.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
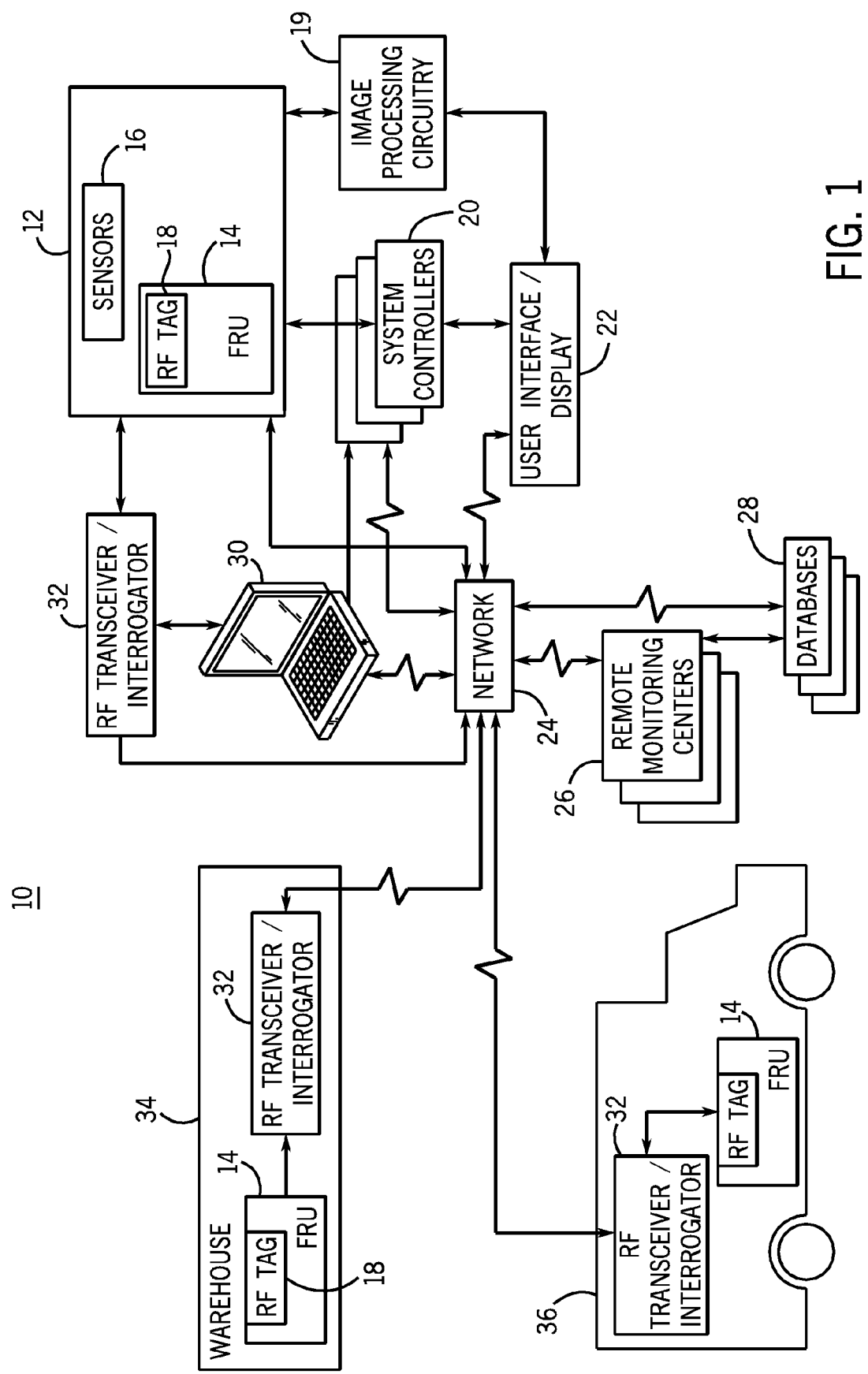
FIG. 1 is a diagrammatical illustration of an exemplary imaging network in accordance with aspects of the present technique.

Turning to the drawings, FIG. 1 illustrates an exemplary imaging device system 10. Although reference is made to imaging devices throughout the following discussion, this is not to be viewed as limiting the present technique to imaging devices. Medical devices, such as heart and other monitors, surgical instruments, devices for administration or regulation of medicament or other flows, endoscopic devices, to name but a few types of medical devices, may benefit from the present technique. Indeed, the present technique is applicable to any number of medical devices, and imaging devices are just but one example. The exemplary system includes an imaging device 12, such as a magnetic resonance imaging (MRI) scanner, a computed tomography (CT) scanner, an X-ray device, a mammography device, to name but a few kinds of imaging devices. When installed at a medical facility, the imaging device 12 provides image data and reconstructed images of a patient. The imaging device 12 may include any number of components, many of which may be field replaceable units or FRUs 14. Examples of such FRUs include sensors 16. Certain, or all FRUs 14 may include, in accordance with the present technique, RF tags 18, as discussed in further detail below.

To produce image data and reconstructed images from the raw data regarding the patient (e.g., resulting from attenuation of a beam of X-ray radiation by internal anatomies of a patient, the imaging device 12 may transmit this raw data to image processing circuitry 19. By way of example, the image processing circuitry 19 may include a digital-to-analog converter (DAC) that receives analog signals and converts them to digital signals via digital signal processing (DSP) circuits.

One or more system controllers 20 may direct and control operation of the imaging device 12. By way of example, the system controllers 20 may comprise processor-based devices or programmable logic units (PLUs), both of which may analyze data from the sensors 16 located throughout the imaging device 12 and may provide commands or instructions for operation of the device. For automated control of the imaging device 12, computer programs typically provide instructions to the various system controllers 20. The computer programs also may interpret data from the various sensors 16 and provide appropriate instructions in response.

Both the image processing circuitry 19 and the system controllers 20 may communicate with a user interface 22. By way of example, the user interface 22 may include a display for presenting the produced image to a medical professional for diagnostic purposes. Moreover, the user interface 22 may receive inputs from the user and may communicate such inputs to the imaging device 12 or system controller, for example.

In many instances, the imaging device 12 may communicate with remote locations and devices via a network 24, such as a Local Area Network (LAN), a Server Area Network (SAN), a Metropolitan Area Network (MAN), a Wide Area Network (WAN), a Virtual Private Network (VPN), the Internet, or any other suitable kind of network. Communications over the network 24 may be conducted via any number of communications schemes and protocols, such as Global Standard for Mobile (GSM), Time Division for Multiple Access (TDMA), Code Division Multiple Access (CDMA), Frequency Division Multiple Access (FDMA), or any other suitable communications techniques. By way of example, the imaging system 10 may communicate with one or more remote monitoring centers 26, which may receive operation data and imaging data from the imaging device 12 via the network 24. Advantageously, the remote monitoring centers 26, communicating via the network 24, may improve the image data quality as well as remotely monitor and adjust the operating parameters of the imaging device 12. The network 24 may also facilitate access to remote databases 28. Advantageously, the remote databases 28 may store large volumes of data and data from a wide variety of sources coupled to the network 24. That is, data from multiple imaging devices 12 may be stored at a central location. Indeed, such data may be accessed by user interfaces 22 at locations remote from the imaging device 12 that produced the data.

In certain instances, a field technician may wish to access data or alter operating parameters related to the imaging device 12. Accordingly, a field unit 30, such as a laptop computer or hand-held device, may communicate with the system controllers 20. Advantageously, the field technician, via the field unit 30, may monitor operations of the imaging device 12 and provide system adjustments in response, to improve the quality of the images produced or otherwise to service operation of the system. Furthermore, the field technician may remotely access data regarding the operations of the imaging device 12 for purposes of testing and calibration, for example. Moreover, the field unit 30 also may communicate with the imaging device 12, the databases 28, and remote monitoring centers 26 via the network 24.

As discussed above, the imaging device 12 may include a number of components configured for operation with the imaging device 12. In many instances, the components may be field replaceable units or FRUs 14. That is, the component may be serviceable and replaceable while the imaging device 12 is at its operating location, such as a medical facility. By way of example, the FRU 14 may include a compressor, a cold head, a gantry component, a printed circuit board, to name but a few categories or types of FRUs 14. Moreover, it is worth noting again that components of medical devices unrelated to imaging devices also may fall within the scope of the present application. As stated above, imaging devices are just but one exemplary type of medical device. Each or certain of the FRUs 14 may include an RF tag 18. As discussed further below, the RF tag 18 may contain information regarding the FRU 14, more particularly, information regarding maintenance, manufacture, and installation of the FRU 14.

To receive the information from the RF tags 18, the system 10 may include an RF transceiver 32. For example, the RF transceiver 32 may accept and interpret RF transmissions from the RF tags 18. In certain instances, the RF transceiver 32 may include an interrogator. Advantageously, the interrogator may activate the RF tag 18, thereby allowing the RF transceiver 32 to receive the transmissions from the RF tag 18, as discussed further below. The RF transceiver 32 may communicate with remote locations, such as the database 28 and the remote monitoring centers 26, via the network 24. Moreover, the RF transceiver 32 may communicate with local devices, such as the field unit 30 or the user interface 22, which is typically local to the transceiver. The workings of the RF tag 18 and the RF transceiver 32 are discussed in further detail below.

Prior to installation, however, the FRUs 14 may be stocked at a storage facility, such as a warehouse 34, or at a mobile location, such as in the possession of a mobile service provider 36. Accordingly, as discussed further below, RF transceivers 32 and interrogators may survey the FRUs 14 located at these locations for desirable information. For example, the FRUs may be surveyed to determine how many FRUs of a certain lot number are still within inventory. Advantageously, this information may be communicated to other locations via the network 24.

Figure 2:
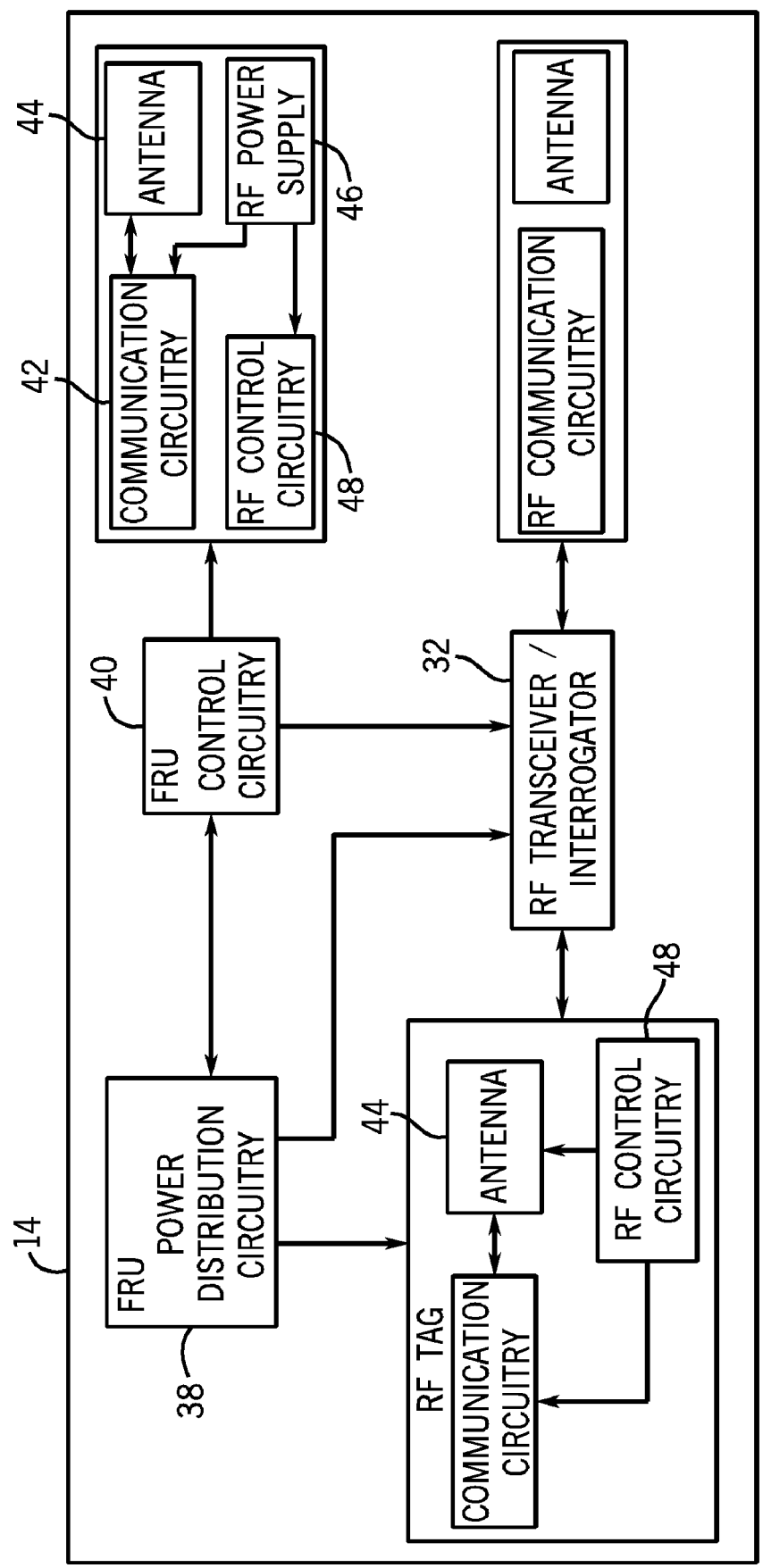
FIG. 2 is a diagrammatical illustration of an exemplary imaging device component in accordance with aspects of the present technique.

FIG. 2 is a block diagram of an exemplary FRU 14. The FRU 14 may receive power from a local power source, such as a battery, or from a distributed power source, such as the power source of the imaging device 12. To distribute this power, the FRU 14 may include power distribution circuitry 38. Advantageously, the power distribution circuitry 38 of the FRU may include signal-conditioning circuitry, which may condition the received power to appropriate levels for the various devices within the FRU 14. For example, the power distribution circuitry may rectify ac power to dc power, as required. The FRU 14 also may include control circuitry 40 that provides commands to the various devices within the FRU 14. For example, the FRU control circuitry 40 may provide commands to and receive data from the RF transceiver 32. Advantageously, the FRU control circuitry 40 may communicate with the system controllers 20 (see FIG. 1) of the imaging device 12. Accordingly, the system controllers 20, through the FRU control circuitry 40, may command the various devices of the FRU 14. For example, the system controllers 20 may provide commands to a RF transceiver 32 located in the FRU 14.

As discussed above, the exemplary FRU 14 includes RF tags 18. If so desired, the RF tags 18 may be integrated with the respect to the FRU 14 or may be coupled to the FRU 14 externally. The RF tag 18 will typically include communications circuitry 42 coupled to an antenna 44. The communications circuitry 42 may store information related to the component and may transmit this information, via the antenna 44, to an appropriate reading device, such as the RF transceiver 32. Indeed, the communications circuitry 42 may be an integrated circuit that is relatively small in size.

As one example, the RF tag 18 may be an active tag. That is, the RF tag 18 may receive a steady source of power from a power supply, such as the FRU power distribution circuitry 38 or an independent RF power supply 46, such as a battery. The RF tag 18 may include RF control circuitry 48, which may control operations of the RF tag 18, e.g., control transmissions from the RF tag 18. Indeed, constant transmission of an RF signal by the RF tag 18 may interfere with operations of the imaging device 12 (see FIG. 1). Accordingly, the RF control circuitry 48 may activate and deactivate the communications circuitry 42 to prevent interference with operations of the imaging device 12. Advantageously, the RF control circuitry 48 may communicate with the FRU control circuitry 40, which, in turn, communicate with the systems controllers 20. Accordingly, the command to activate or deactivate the RF tag 18 may come from any number of locations, e.g., the remote control centers 26, the user interface 22, and so forth.

Alternatively, the RF tag 18 may be a passive tag. That is, a low-level radio frequency electro-magnetic field generated by the RF transceiver 32 (more specifically, an interrogator of the RF transceiver) may power the RF tag 18. Accordingly, when the RF transceiver 32 generates the appropriate field, the RF tag 18 may begin to broadcast the information stored therein. Because the RF tag 18 does not broadcast when unpowered by the appropriate field, it remains dormant (i.e., not broadcasting) during operation of the imaging device 12 (see FIG. 1). Thus, the RF tag 18 does not interfere with operation of the imaging device 12.

Figure 3:
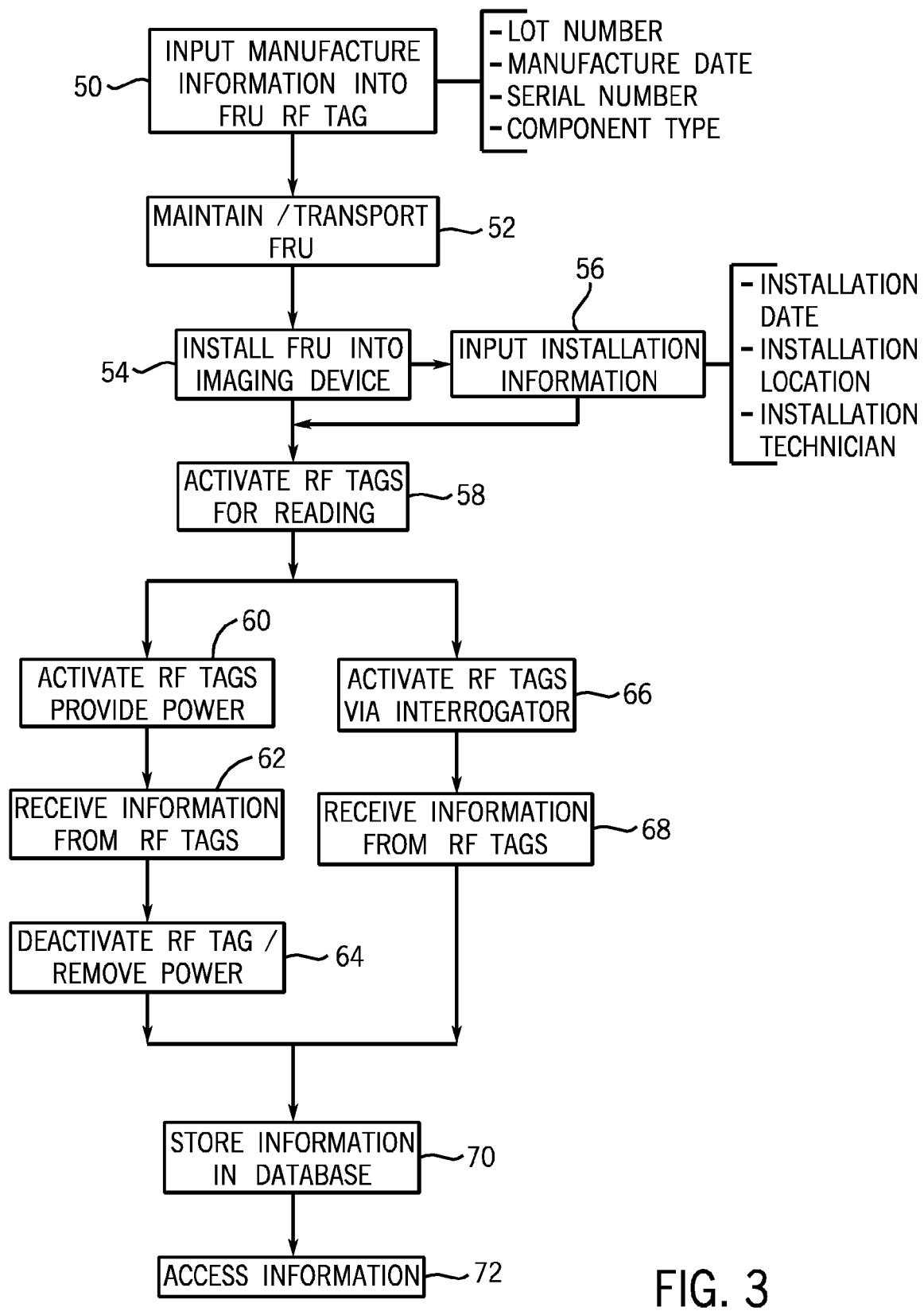
FIG. 3 is a flow chart of an exemplary process in accordance with aspects of the present technique.

FIG. 3 illustrates an exemplary process for providing information regarding the FRU 14. The exemplary process includes inputting manufacture information into the RF tag 18. For example, the manufacturer may enter the FRU 14 lot number, manufacture date, serial number, component type, component specifications, to name but a few types of manufacture information. Block 50 represents this step in the exemplary process. The exemplary process also includes maintaining and transporting the FRU 14, as represented by block 52. For example, the FRU 14 may be maintained at the warehouse 34 for initial installation. Alternatively, the FRU 14 may be in the possession of the mobile service technician 36 for installation at the operating location, e.g., at the medical facility. Advantageously, by reading the transmissions from the RF tags 18, a current inventory of the FRUs at the exemplary locations may be determined.

In either event, the FRU 14 may be installed into the imaging device 12, as represented by block 54. Once installed, information related to installation of the component may be entered into the RF tag 18. For example, a technician may enter an installation date, installation location, installation technician, to name but a few types of installation information, into the RF tag 18. Block 56 represents this step in the exemplary process. Moreover, if maintenance has been conducted on the component, this information may also be entered into the RF tag 18. For example, if the technician has recalibrated or restored the FRU 14 to operating status, the technician may enter this maintenance information into the RF tag 18.

When appropriate, the maintenance, installation and/or manufacture information related to the FRU 14 stored in the RF tag 18 may be retrieved. To accomplish this, a technician may activate the RF tags 18 for reading, as represented by block 58. This task may vary depending upon the type of RF tag 18 employed, i.e., passive or active. For example, to activate an active RF tag 18, the technician may provide power to the communication circuitry via a power source, such as a battery in the RF tag itself or from power distribution circuitry within the FRU. Block 60 represents these steps in the exemplary process.

The activated RF tags 18, i.e., the RF tags 18 receiving power, may broadcast the information stored in the RF tag 18. The RF transceiver 32 may receive this information and provide it to the appropriate location. For example, the RF transceiver 32 may provide the information to the system controllers 20, the field unit 30 or to remote locations connected to the network 24. Block 62 represents this step in the exemplary process. To prevent the RF transmissions from the RF tag 18 from interfering with operations of the imaging device 12, power may be removed, thereby deactivating the RF tags 18, as represented by block 64. That is, upon removal of the power from the RF tag 18, the RF tag may deactivate and may cease broadcasting any RF transmissions. Accordingly, the RF tags 18 may be activated when the imaging device is not in use, such as during startup or just prior to servicing.

Alternatively, the RF tags 18 may be passive RF tags 18. Accordingly, providing a low-level radio frequency electromagnetic field generated by the interrogator device of the RF transceiver 32, for example, may activate the RF tags 18. Block 66 represents this step in the exemplary process. Once activated, the RF transceiver 32 may receive the RF transmissions that may contain maintenance, installation, and manufacture information form the RF tags 18, as represented by block 68. Because the RF tags 18 are passive, removing the electrical field generated by the interrogator deactivates the passive RF tags 18.

In either case, the obtained information may be stored in databases, such as the remote databases 28. Accordingly, the stored information may be accessed by technicians for any number of purposes, examples of which are discussed further below. Blocks 70 and 72 represent these steps in the exemplary process. Advantageously, a component list of the imaging device 12 may be developed without considerable expense and the tedium of paperwork. For example, if a technician wished to obtain an "as built" configuration (i.e., current hardware configuration) of an imaging device 12 at a certain medical facility, he could activate the RF tags 18 and receive the transmitted information, because each RF tag 18 holds information regarding its respective components, e.g., FRUs 14. Indeed, various components may be interchanged and replaced by any number of technicians, and an "as built" list may be obtained by activating the RF tags and reading the information stored therein. Moreover, by way of example, the integrated relationship between the RF tag 18 and the FRU 14 may provide easily accessible information regarding the FRUs 14 in the imaging device 12 even without an affirmative action by the technician.

Advantageously, because of the interconnectivity of the network, the system controllers, the FRU control circuitry, and the RF control circuitry, the foregoing steps may be performed remotely. For example, a technician located at the remote monitoring center 26 may activate the RF tags 18 to obtain the information stored in the RF tags 18. Furthermore, a computer program, remotely or locally located, may command the various devices of the imaging device system 10 to conduct the exemplary steps discussed above.

Figure 4:
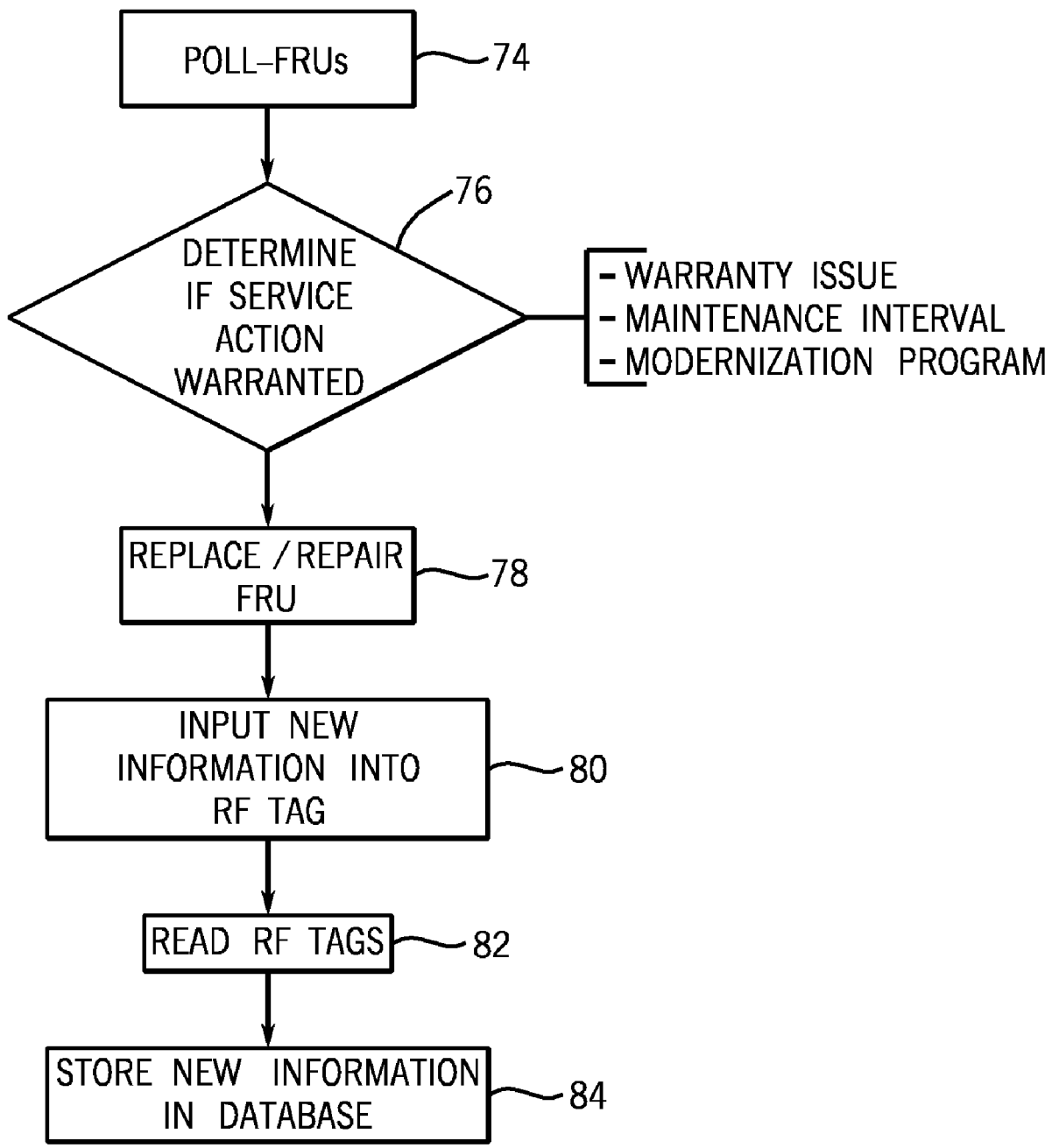
FIG. 4 is a flow chart of another exemplary process in accordance with aspects of the present technique.

FIG. 4 represents steps in an exemplary process for maintaining and/or servicing an imaging device 12. As one step, the technician may poll or survey the FRUs 14 in the imaging device 12. For example, the technician may carry a hand-held RF transceiver 32 into proximity with the imaging device 12. Once there, he may activate the RF tags 18 and receive the information broadcast by the RF tags 18. Of course, because of the connectivity of the imaging device system 10, the technician may conduct this step from a remote location. Block 74 represents this step in the exemplary process.

With the FRU information obtained from the RF tags 18, the technician may determine whether service or maintenance of the imaging device 12 or FRU 14 is warranted, as represented by block 76. For example, if a certain type of FRU 14 has been recalled, it may be difficult to determine at what locations such FRUs 14 are installed. However, by surveying imaging devices 12 at various locations via the RF tags 18 coupled to the appropriate FRUs 14, an "as built" list may be quickly determined. With the "as built" information, the technician may determine if the FRUs 14 at the imaging device he is presently servicing require replacing. As another example, the FRU 14 may require servicing a various intervals. However, various FRUs 14 may have been installed into the imaging device 12 at different times by different technicians. Accordingly, by surveying the imaging device 12 via the RF tags 18, the installation information may indicate when the particular FRU was installed, from which the time until probable lapse of the maintenance interval may be determined. As yet another example, a modernization program to replace FRUs in need of frequent repair may employ the RF tags 18. Because the RF tag 18 may contain information regarding maintenance of the FRU 14, a technician may simply survey the RF tags 18 and determine when the various FRUs have been serviced and what service was conducted.

In any event, the technician may repair or replace the FRU 14, as represented by block 78. Once the FRU 14 has been replaced or repaired, if desired, the technician may enter new information into the RF tag 18 of the replaced or repaired FRU 14. Alternatively, the information may be inserted into the RF tag from a remote location via the network, for example. That is, the information may be "pushed" onto the RF tag 18 from a remote location. Block 80 represents these steps in the exemplary process. The exemplary process also may include reading the RF tags 18 that contain information regarding the FRU 14 to determine the changes made by the technician and for storage of the FRU information into the databases 28, as represented by blocks 82 and 84.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims. Indeed, the present technique may benefit any number of medical devices, of which imaging devices are but one exemplary kind.

The invention claimed is:

1. A system in combination with an imaging device, the imaging device having a plurality of components that in operate in combination to acquire an image, the system comprising:

a radio frequency (RF) transmitter operable to communicate an information regarding one of the plurality of components of the imaging device; and a RF receiver in communication to receive the information from the RF transmitter, wherein the RF transmitter is prevented from communicating the information during acquisition of an image by the medical device.

2. The system as recited in claim 1, wherein one of the plurality of components of the imaging device includes a field replaceable unit, and wherein the RF transmitter communicates the information regarding one of the field replaceable unit in response to a command from the imaging device.

3. The system as recited in claim 1, further comprising a RF interrogator, wherein the RF transmitter transmits the information in response to a signal from the RF interrogator.

4. The system as recited in claim 1, wherein the RF transmitter comprises a power source.

5. The system as recited in claim 1, wherein the RF transmitter receives electrical power from one of the plurality of components of the medical device.

6. The system as recited in claim 1, wherein the RF transmitter is prevented from communicating the information in response to detection of acquisition of images by the imaging device.

7. The system as recited in claim 1, wherein the RF transmitter does not receive electrical power so as to prevent communicating the information during acquisition of images by the medical device.

8. The system as recited in claim 1, wherein the RF transmitter communicates the information in response to a signal from one of the plurality of components of the imaging device.

9. An imaging device, comprising:

a plurality of components operable in combination to acquire an image;

a radio frequency (RF) transmitter in communication to receive an information from at least one of the plurality of components of the imaging device; and a RF receiver configured to receive the information from the RF transmitter, wherein the RF transmitter does not broadcast during acquisition of the image by the imaging device.

10. The imaging device as recited in claim 9, wherein the imaging device is one of a group comprising: a magnetic resonance imaging device, a computed tomography imaging device, an x-ray imaging device, and a mammography imaging device.

11. The imaging device as recited in claim 9, further comprising an RF interrogator, wherein the RF transmitter is configured to transmit the information regarding one of the plurality of components in response to a signal from the RF interrogator.

12. The imaging device as recited in claim 9, wherein the RF transmitter communicates the information regarding one of the plurality of components of the imaging device in response to a command from the imaging device.

13. The imaging device as recited in claim 9, wherein the RF transmitter comprises a power source.

14. The imaging device as recited in claim 9, wherein the RF transmitter receives electrical power from one of the plurality of components of the imaging device.

15. The imaging device as recited in claim 9, further including an interface in communication with the RF transmitter, wherein the RF transmitter receives a signal from the interface to prevent transmitting the information regarding one of the plurality of components of the imaging device.

16. The imaging device as recited in claim 9, wherein the information regarding one of the plurality of components includes one or more of the group comprising:
   a manufacture date, a component list, a serial number, a component type, a component specification, an installation date, an installation location, an installation technician, date of repair, and date of replacement.

17. A method to maintain an imaging device having a plurality of components operable in combination to acquire an image , the method comprising the steps of:
   communicating an information regarding one of the plurality of components via a transmission from a radio frequency (RF) device; and
   inactivating the RF device so as not to communicate the information when the imaging device is in operation to acquire an image.

18. The method of claim 17, wherein the communicating step includes communicating power to the RF device from the field replaceable unit of the medical imaging device, and wherein the inactivating step includes not communicating power to the RF device in response to detecting operation of the imaging device to acquire an image.

19. The method as recited in claim 17, wherein the communicating step includes receiving electrical power at the radio frequency (RF) device from one of the plurality of components of the imaging device.

20. The method as recited in claim 17, further including communicating a signal from an interface in communication with the RF transmitter, wherein the signal from the interface to the RF transmitter prevents transmitting the information regarding one of the plurality of components of the imaging device.

21. The method as recited in claim 17, wherein the inactivating step includes not communicating the information regarding one of the plurality of components of the imaging device until receiving a signal from the imaging device.

* * * * *